(12) United States Patent
Mamedov et al.

(10) Patent No.: US 8,013,198 B2
(45) Date of Patent: Sep. 6, 2011

(54) PROCESS FOR SIMULTANEOUS PRODUCTION OF BENZENE AND ETHYLENE BY CONVERSION OF ACETYLENE

(75) Inventors: Agaddin Mamedov, Houston, TX (US); Tony Joseph, Riyadh (SA); Mohamed Al-Otaibi, Riyadh (SA)

(73) Assignee: Saudi Basic Industries Corporation, Riyadh (SA)

( * ) Notice: Subject to any disclaimer, the term of this patent is extended or adjusted under 35 U.S.C. 154(b) by 522 days.

(21) Appl. No.: 11/886,888

(22) PCT Filed: Feb. 22, 2006

(86) PCT No.: PCT/IB2006/000357
§ 371 (c)(1),
(2), (4) Date: Feb. 2, 2009

(87) PCT Pub. No.: WO2006/100549
PCT Pub. Date: Sep. 28, 2006

(65) Prior Publication Data
US 2009/0287031 A1    Nov. 19, 2009

(30) Foreign Application Priority Data
Mar. 23, 2005 (EP) .................................... 05006438

(51) Int. Cl.
*C07C 15/00* (2006.01)
*C07C 5/05* (2006.01)
(52) U.S. Cl. ................... 585/416; 585/271; 585/943
(58) Field of Classification Search ............... 585/416, 585/271, 943
See application file for complete search history.

(56) References Cited

U.S. PATENT DOCUMENTS

| 1,868,127 | A | 7/1932 | Winkler et al. |
| 2,723,299 | A | 11/1955 | Tanaka et al. |
| 4,350,835 | A | 9/1982 | Chester et al. |
| 4,392,989 | A | 7/1983 | Chu et al. |
| 4,424,401 | A | 1/1984 | White et al. |
| 5,118,893 | A | 6/1992 | Timmons et al. |

FOREIGN PATENT DOCUMENTS

| GB | 211461 A | 11/1924 |
| GB | 301325 A | 11/1929 |

OTHER PUBLICATIONS

Dingjun Wang et al.; Characterization of a Mo/ZSM-5 Catalyst for the Conversion of Methane to Bernzene; Jour of Cat, vol. 169, p. 347-358, 1997.
Jin Long Zeng et al.; Nonoxidative Dehydrogenation and Aromatization of Methane Over W/HZSM-5-based Catalysts; Cat Letters 53, p. 119-124 (1998).
Abdel-Ghani Boudjahem et al; Acetylene Cyclotrimerization Over Ni/SiO2 Catalysts in Hydrogen Atmosphere; Applied Cat A: General, 2003, p. 49-64, vol. 250.

*Primary Examiner* — Thuan Dinh Dang
(74) *Attorney, Agent, or Firm* — Cantor Colburn LLP

(57) ABSTRACT

The present invention relates to a process for simultaneous production of benzene and ethylene by conversion of acetylene, comprising the steps: supplying a feed composition comprising about 5 to about 30 vol-% acetylene, about 5 to about 30 vol-% methane, about 5 to about 30 vol-% carbon dioxide and about 10 to about 70 vol-% hydrogen into a non-metallic reactor; and thermally reacting the feed composition in the reactor at a temperature in the range of about 600 to about 1000° C.

9 Claims, No Drawings

PROCESS FOR SIMULTANEOUS PRODUCTION OF BENZENE AND ETHYLENE BY CONVERSION OF ACETYLENE

The present invention relates to a process for simultaneous production of benzene and ethylene by conversion of acetylene.

Several processes for the production of benzene are known, for example production from catalytic reformat, production from gasoline pyrolysis, production by toluene conversion or production by LPG aromatization, see for example U.S. Pat. No. 4,350,835 or U.S. Pat. No. 4,392,989.

One further process for benzene formation is the methane aromatization on zeolite-containing catalysts. Several articles were published on non-oxidative methane aromatization on zeolite-based catalysts, for example J. Catal, 169, 347 (1977); Cat. Lett. 53 (1998) 119.

U.S. Pat. No. 4,424,401 describes the aromatization of acetylene to a mixture of hydrocarbons in the presence of zeolite catalyst ZSM-5. The acetylene aromatization was conducted with dilution of acetylene with inert gases, water, hydrogen, methane and alcohols. The reaction was carried out by using ZSM-5 type zeolite having a silica to alumina molar ratio of 100 at a temperature in the range of 260 to 550° C. to convert acetylene to a mixture of aromatic hydrocarbons.

Another process for benzene formation is the conversion of acetylene to benzene, as for example disclosed in Appl. Cat. A. General. 250 (2003) 49-64. U.S. Pat. No. 5,118,893 discloses a catalytic conversion of acetylene to aromatics in the presence of Ni or Co containing catalysts with the addition of hydrogen to the acetylene feed.

Unfortunately, the process of methane or acetylene aromatization on zeolites or other catalysts has a lot of disadvantages. The catalysts show a very short time of performance and rapid deactivation due to the accumulation of coke fragments. Further, high amounts of other by-products from acetylene conversion are formed. Additionally, the formation of coke fragments inside of channels of the zeolites leads to a decrease of catalyst stability.

Aromatization of acetylene to aromatics is also known from U.S. Pat. No. 1,868,127, and this reaction was conducted by heating of acetylene to temperatures above 400° C. A variety of products were produced by this process including benzene, styrene, naphthalene and higher aromatics.

It is an object of the present invention to provide a process for simultaneous production of benzene and ethylene overcoming the drawbacks of the prior art, especially to provide a high conversion of acetylene and high yields of benzene and ethylene without using a catalyst.

The object is achieved by a process for simultaneous production of benzene and ethylene by conversion of acetylene, comprising the steps: supplying a feed composition comprising about 5 to about 30 vol-% acetylene, about 5 to about 30 vol-% methane, about 5 to about 30 vol-% carbon dioxide and about 10 to about 70 vol-% hydrogen into a non-metallic or ceramic reactor; and thermally reacting the feed composition in the reactor at a temperature in the range of about 600 to about 1000° C. The inventive process is preferably carried out under non-isothermal conditions.

Preferably, the feed composition comprises about 10 to about 25 vol-% acetylene, about 10 to about 25 vol-% methane, about 10 to about 25 vol-% carbon dioxide and about 40 to about 70 vol-% hydrogen is supplied into the reactor.

The invention process may further comprise most preferably supplying a feed composition comprising about 13 to about 18 vol-% acetylene, about 13 to about 18 vol-% methane, about 15 to about 25 vol-% carbon dioxide and about 45 to about 60 vol-% hydrogen is supplied into the reactor.

In one embodiment, the temperature is in the range of about 800 to about 950° C.

Preferably, the residence time of the feed composition in the reactor is from about 0.5 to about 10 seconds.

More preferably, the space velocity of the feed composition is from about 400 to about 5000 $h^{-1}$, preferably about 1800 to about 3000 $h^{-1}$.

The space velocity is an important factor affecting the benzene/ethylene ratio. A high space velocity gives high ethylene yield whilst a low space velocity gives high benzene yield.

Preferably, the reactor is a quartz or ceramic reactor.

In a further and most preferably embodiment the reactor is a tubular reactor.

Moreover, it is preferred that the internal diameter of the tubular reactor is from about 4 to about 15 mm, preferably about 4 mm.

Finally, the process is preferably continuous, semi-continuous or discontinuous.

Surprisingly, it was found that utilizing the process according to the present invention benzene and ethylene may be simultaneously produced by a thermal aromatization of acetylene in the presence of suitable compounds, namely hydrogen, methane and carbon dioxide utilizing suitable reaction conditions and a specific reactor.

It was found that the partial pressure of methane is important for achieving high benzene selectivity. Partial pressure of methane is regulated by carbon dioxide which besides dilution has also properties of reactant regulating coke amount through in situ reaction with coke fragments.

It was found in detail that in the feed composition used in the inventive process the presence of methane is effective for decreasing of coke formation in equilibrium reaction:

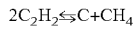

$$2C_2H_2 \leftrightarrows C + CH_4$$

The participation of hydrogen is also necessary for decreasing of coke fragments in acetylene decomposition reaction:

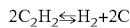

$$2C_2H_2 \leftrightarrows H_2 + 2C$$

Further, it was found, that at very high concentrations of hydrogen, the hydrogenolysis of acetylene takes place:

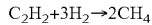

$$C_2H_2 + 3H_2 \rightarrow 2CH_4$$

Because of this reason some amount of hydrogen in the feed composition was substituted by carbon dioxide which regulates the acetylene concentration in the feed composition and decreases coke formation.

A most preferred mixture to be supplied in the process of the present invention comprises about 15 vol-% acetylene, about 15 vol-% methane, about 20 vol-% carbon dioxide and about 50 vol-% hydrogen. Using more than 30 vol-% acetylene will result in the fact that coke selectivity will be too high. If a mixture is utilized containing less than 5 vol-% of acetylene, the resulting benzene and ethylene concentrations are very low.

The process according to the present invention is preferably carried out in a ceramic or quartz reactor. In metallic reactors, acetylene conversion proceeds in the direction of a deep decomposition of acetylene with formation of hydrogen and coke fragments only.

Preferably, the reactor has an internal diameter of about 4 to about 15 mm, preferably 4 mm, wherein the reaction may be carried out in furnaces with 13 and 45 cm length, using, for example, three-zone furnaces with 45 cm length under variation of the L/D parameter of the reactor (L-reactor length, D-reactor diameter). However, it was found that the benzene yield obtained in a three-zone furnace is less in comparison with a single zone furnace. A three-zone furnace is a standard equipment used in catalysis work wherein the three zones are heated separately in order to maintain isothermal conditions throughout the reactor length. As illustrated in the examples section below, the results obtained in a single zone furnace are better than the ones obtained in the three-zone furnace.

The process of the present invention may be advantageously employed as a second stage of methane thermal aromatization to benzene, wherein in the first stage methane is converted to acetylene. There is extensive research for converting of methane to acetylene. For example, U.S. Pat. No. 6,323,247 discloses a process of thermal conversion of acetylene, wherein the acetylene yield is 76%. Thus, using the inventive process as a second stage makes the two step process of methane conversion to benzene and ethylene via acetylene a possible alternative process.

Additional features and advantages of the process of the present invention are given in the following detailed description of comparative examples and examples according to the present invention.

The following examples are intended to be illustrative for this invention only. They are, of course, not be taken in any way as limiting on the scope of the invention. Numerous changes and modifications can be made with respect to the invention.

EXAMPLES

The reaction conditions and process parameters are illustrated in the following examples and comparative examples.

Comparative Example 1

The conversion of acetylene to benzene and ethylene was carried out in a quartz reactor having an internal diameter of 10 mm; a feed composition was supplied to the reactor containing 20 vol-% acetylene and 80 vol-% methane. The reaction temperature was varied. The results are given in the table 1 below, indicating that only low benzene and ethylene selectivities are obtained, whereas the selectivity for coke fragments and methane is significantly high.

TABLE 1

The conversion of acetylene in quartz reactor with 10 mm; reaction mixture 20% CH2 + 80% CH4

| | TEMPERATURE, °C. | | | | |
|---|---|---|---|---|---|
| | 600 | 625 | 650 | 670 | 700 |
| Feed Total flow rate, cc/min | 10 | 10 | 10 | 10 | 10 |
| C2H2, cc/min | 2 | 2 | 2 | 2 | 2 |
| CH4, cc/min | 8 | 8 | 8 | 8 | 8 |
| Space velocity, h$^{-1}$ | 511 | 526 | 540 | 552 | 570 |
| C2H2 conversion | 62.2 | 78.0 | 89.0 | 93.0 | 97.6 |
| C6H6 selectivity | 24.0 | 20.2 | 21.8 | 21.3 | 22.2 |
| C2H4 selectivity | 5.5 | 6.0 | 7.4 | 10.1 | 9.7 |
| Coke + CH4 sel., % | 70.5 | 73.8 | 70.8 | 68.6 | 68.1 |
| C6H6 Yield | 14.9 | 15.6 | 19.4 | 19.5 | 21.7 |
| C2H4 Yield | 3.4 | 4.7 | $^{1}$6.5 | 9.3 | 8.8 |

Comparative Example 2

Comparative example 2 was carried out in the same manner as comparative example 1, however, the total flow rate was varied. As can be seen from the results given in the table below, only low benzene and ethylene selectivities, but high coke and methane selectivities are obtained.

TABLE 2

| | TEMPERATURE, °C. | | | |
|---|---|---|---|---|
| | 700 | 600 | 600 | 700 |
| Feed Total flow rate, cc/min | 10 | 20 | 30 | 30 |
| C2H2, cc/min | 2 | 4 | 6 | 6 |
| CH4, cc/min | 8 | 16 | 24 | 24 |
| Space velocity, h$^{-1}$ | 570 | 1023 | 1530 | 1710 |
| C2H2 conversion | 97.6 | 45.8 | 67.4 | 88.0 |
| C6H6 selectivity | 22.2 | 28.9 | 22.9 | 28.4 |
| C2H4 selectivity | 9.7 | 5.6 | 6.4 | 10.3 |
| Coke + CH4 sel., % | 68.1 | 65.5 | 70.7 | 61.3 |
| C6H6 Yield | 21.7 | 13.2 | 15.4 | 24.6 |
| C2H4 Yield | 8.8 | 2.5 | 4.3 | 9.1 |

Comparative Example 3

Comparative example 3 illustrates a process for acetylene conversion utilizing acetylene and methane as feed mixture, wherein the process is carried out in a quartz reactor having an internal diameter of 4 mm.

TABLE 3

| | TEMPERATURE, °C. | | | |
|---|---|---|---|---|
| | 800 | 850 | 900 | 850 |
| Feed Total flow rate, cc/min | 25 | 25 | 25 | 30 |
| C2H2, cc/min | 5 | 5 | 5 | 6 |
| CH4, cc/min | 20 | 20 | 20 | 24 |
| Space velocity, h$^{-1}$ | 1572 | 1645 | 1718 | 1645 |
| C2H2 conversion | 87.0 | 97.6 | 98.6 | 90.0 |
| C6H6 selectivity | 27.5 | 31.6 | 30.8 | 36.8 |
| C2H4 selectivity | 12.6 | 15.2 | 9.97 | 14.3 |
| Coke + CH4 sel., % | 27.4 | 50.8 | 59.3 | 55.1 |
| C6H6 Yield | 23.9 | 30.8 | 30.4 | 33.2 |
| C2H4 Yield | 10.9 | 14.8 | 9.8 | 12.5 |

Comparative Example 4

Comparative example 4 illustrates a process wherein as an additional feed component hydrogen is utilized. The feed composition supplied to the reactor contained 20 vol-% acetylene, 20 vol-% methane and 60 vol-% hydrogen. A quartz reactor having an internal diameter of 4 mm was used. As can be seen from the results given in table 4 below, also the use of hydrogen may not significantly improve the benzene and ethylene selectivities and further provides a high selectivity with regard to coke and methane formation.

TABLE 4

| | TEMPERATURE, °C. | | | | | |
|---|---|---|---|---|---|---|
| | 850 | 870 | 860 | 880 | 890 | 900 |
| Feed Total flow rate, cc/min | 30 | 30 | 37 | 37 | 45 | 45 |
| C2H2, cc/min | 6 | 6 | 7.4 | 7.4 | 9 | 9 |
| CH4, cc/min | 6 | 6 | 7.4 | 7.4 | 9 | 9 |

TABLE 4-continued

| | TEMPERATURE, °C. | | | | | |
|---|---|---|---|---|---|---|
| | 850 | 870 | 860 | 880 | 890 | 900 |
| H2, cc/min | 18 | 18 | 22.2 | 22.2 | 27 | 27 |
| Space velocity, $h^{-1}$ | 1974 | 2009 | 2456 | 2500 | 3067 | 3093 |
| C2H2 conversion | 95 | 95 | 96.9 | 96.5 | 96.2 | 95.8 |
| C6H6 selectivity | 29.2 | 28.5 | 28.7 | 28.7 | 36.9 | 40.9 |
| C2H4 selectivity | 21.5 | 22.0 | 20.9 | 21.2 | 20.0 | 19.5 |
| Coke + CH4 sel., % | 32.4 | 35.6 | 33.12 | 24.6 | 31.7 | 28.3 |
| C6H6 Yield | 27.7 | 27.1 | 27.8 | 27.7 | 35.6 | 39.1 |
| C2H4 Yield | 20.3 | 20.4 | 20.3 | 20.5 | 19.3 | 18.7 |

Comparative Example 5

Comparative example 5 illustrates the effect of the flow rate with a feed composition containing 15 vol-% acetylene, 30 vol-% methane and 55 vol-% hydrogen. The reactor used had an internal diameter of 4 mm. Again, high selectivities for coke and methane are obtained resulting in a less economic process.

TABLE 5

| | TEMPERATURE, °C. | | | | | | | | |
|---|---|---|---|---|---|---|---|---|---|
| | 750 | 840 | 880 | 900 | 860 | 915 | 880 | 900 | 915 |
| Feed Total flowrate, cc/min | 30 | 30 | 30 | 30 | 40 | 40 | 50 | 50 | 50 |
| C2H2, cc/min | 4.5 | 4.5 | 4.5 | 4.5 | 6.0 | 6.0 | 7.5 | 7.5 | 7.5 |
| CH4, cc/min | 9.0 | 9.0 | 9.0 | 9.0 | 12.0 | 12.0 | 15.0 | 15.0 | 15.0 |
| H2, cc/min | 16.5 | 16.5 | 16.5 | 16.5 | 22.0 | 22.0 | 27.5 | 27.5 | 27.5 |
| Space velocity, $h^{-1}$ | 1798 | 1956 | 2027 | 2062 | 2749 | 2785 | 3410 | 3437 | 3481 |
| C2H2 conversion | 69.4 | 90.2 | 95.2 | 96.3 | 89.5 | 95.5 | 88.5 | 92.8 | 92.8 |
| C6H6 selectivity | 34.7 | 30.7 | 33.7 | 35.5 | 34.6 | 42.3 | 35.7 | 36.6 | 40.6 |
| C2H4 selectivity | 22.4 | 27.0 | 25.2 | 22.5 | 27.2 | 22.1 | 27.2 | 26.3 | 24.2 |
| Coke + CH4 sel., % | 20.3 | 21.1 | 20.8 | 21.2 | 23.5 | 22.3 | 20.4 | 21.3 | 20.0 |
| C6H6 Yield | 24.1 | 27.7 | 30.6 | 34.2 | 30.4 | 40.2 | 31.6 | 33.4 | 38.1 |
| C2H4 Yield | 15.6 | 24.4 | 24.8 | 21.6 | 24.4 | 21.1 | 23.7 | 24.4 | 22.7 |

Example 6

This example is according to the invention and shows the effect of all feed component, especially carbon dioxide, carbon dioxide in the inventive process in a quartz reactor having an internal diameter of 4 mm. As can be taken from the results illustrated in table 6 below, benzene yields of up to 42 mol-% and ethylene yields of up to 27 mol-% may be obtained, whereas the selectivity for coke and methane is significantly decreased. These results are significantly better than any results described in the literature for ethylene and benzene formation from acetylene, or than the results illustrated in the comparative examples.

TABLE 6

| | TEMPERATURE, °C. | | | | | |
|---|---|---|---|---|---|---|
| | 750 | 800 | 840 | 880 | 900 | 915 |
| Feed Total flow rate, cc/min | 30 | 30 | 30 | 30 | 30 | 30 |
| C2H2, cc/min | 4.4 | 4.4 | 4.4 | 4.4 | 4.4 | 4.4 |
| CH4, cc/min | 4.4 | 4.4 | 4.4 | 4.4 | 4.4 | 4.4 |
| H2, cc/min | 13.2 | 13.2 | 13.2 | 13.2 | 13.2 | 13.2 |
| CO2 cc/min | 8 | 8 | 8 | 8 | 8 | 8 |
| Space velocity, $H^{-1}$ | 1798 | 1886 | 1886 | 2027 | 2036 | 2088 |
| C2H2 conversion, % mole | 69.9 | 79.3 | 84.6 | 92.5 | 94.9 | 95.5 |
| C6H6 selectivity, % mole | 33.3 | 34.6 | 36.5 | 39.7 | 45.0 | 44.6 |
| C2H4 selectivity , % mole | 19.4 | 22.8 | 27.8 | 29.8 | 25.4 | 23.6 |
| Coke + CH4 sel., % mole | 17.1 | 13.6 | 11.2 | 7.7 | 6.9 | 7.3 |
| C6H6 Yield, % mole | 23.3 | 27.4 | 30.9 | 39.7 | 42.7 | 42.6 |
| C2H4 Yield, % mole | 13.6 | 18.1 | 23.5 | 27.5 | 24.1 | 22.6 |

Comparative Example 7

Comparative example 7 illustrates the results of acetylene conversion in a reactor having an internal diameter of 4 mm in a small furnace with 13 cm length. The feed composition was 30 vol-% methane, 15 vol-% acetylene and 55 vol-% hydrogen at different flow rate conditions.

TABLE 7

| | TEMPERATURE, °C. | | |
|---|---|---|---|
| | 920 | 920 | 920 |
| Feed Total flow rate, cc/min | 50 | 30 | 25 |
| C2H2, cc/min | 7.5 | 4.5 | 3.75 |
| CH4, cc/min | 15.0 | 9.0 | 7.5 |
| H2, cc/min | 27.5 | 16.5 | 13.75 |
| Space velocity, $h^{-1}$ | 3495 | 2027 | 1747 |
| C2H2 conversion, % mole | 71.3 | 76.8 | 81.9 |
| C6H6 selectivity, % mole | 21.8 | 27.4 | 33.2 |

TABLE 7-continued

| | TEMPERATURE, °C. | | |
|---|---|---|---|
| | 920 | 920 | 920 |
| C2H4 selectivity, % mole | 25.2 | 30.2 | 35.0 |
| Coke + CH4 sel., % mole | 21.2 | 21.4 | 21.6 |
| C6H6 Yield, % mole | 15.6 | 21.0 | 27.2 |
| C2H4 Yield, % mole | 17.9 | 23.2 | 29.0 |

Comparative Example 8

Comparative example 8 shows the result of acetylene aromatization in a three-zone furnace with variation of temperature.

TABLE 8

| | TEMPERATURE, °C. | | | | | | |
|---|---|---|---|---|---|---|---|
| | 915-462-228 | 900-458-238 | 890-458-233 | 870-375-158 | 890-385-164 | 900-403-180 | 900 single zone |
| Feed Total flow rate, cc/min | 12 | 12 | 12 | 50 | 50 | 50 | 50 |
| C2H2, cc/min | 1.8 | 1.8 | 1.8 | 7.5 | 7.5 | 7.5 | 7.5 |
| CH4, cc/min | 3.6 | 3.6 | 3.6 | 15.0 | 15.0 | 15.0 | 15.0 |
| H2, cc/min | 6.6 | 6.6 | 6.6 | 27.5 | 27.5 | 27.5 | 27.5 |
| L/D (L-reactor length, D-reactor diameter) | 37.5 | 37.5 | 37.5 | 37.5 | 37.5 | 37.5 | 112 |
| C2H2 conversion, % mole | 87.6 | 82.8 | 81.3 | 64.9 | 64.7 | 68.8 | 92.8 |
| C6H6 selectivity, % mole | 25.6 | 24.9 | 24.5 | 24.5 | 22.3 | 21.6 | 36.6 |
| C2H4 selectivity, % mole | 25.0 | 24.3 | 23.3 | 20.7 | 22.8 | 20.7 | 26.3 |
| Coke + CH4 sel., % mole | 14.1 | 15.2 | 16.2 | 31.1 | 25.0 | 20.4 | 21.3 |
| C6H6 Yield, % mole | 22.4 | 20.6 | 19.9 | 15.9 | 14.4 | 14.9 | 33.4 |
| C2H4 Yield, % mole | 21.9 | 20.1 | 19.0 | 13.4 | 14.8 | 14.3 | 24.4 |

The space velocity under such reaction conditions in comparative example 8 is not constant due to the temperature distribution in the reactor.

Comparative Example 9

Comparative example 9 illustrates the conversion of acetylene in a ceramic reactor having an internal diameter of 10 mm using a feed composition of 20 vol-% methane, 20 vol-% acetylene and 60 vol-% hydrogen.

TABLE 9

| | TEMPERATURE, °C. | | | | |
|---|---|---|---|---|---|
| | 700 | 750 | 800 | 830 | 850 |
| Feed Total flow rate, cc/min | 50 | 50 | 50 | 50 | 50 |
| C2H2, cc/min | 10 | 10 | 10 | 10 | 10 |
| CH4, cc/min | 10 | 10 | 10 | 10 | 10 |
| H2, cc/min | 30 | 30 | 30 | 30 | 30 |
| Space velocity, $h^{-1}$ | 1710 | 1798 | 1886 | 1939 | 1974 |
| C2H2 conversion, % mole | 84.4 | 95.0 | 100 | 100 | 100 |
| C6H6 selectivity, % mole | 28.6 | 26.1 | 25.1 | 29.6 | 29.8 |
| C2H4 selectivity, % mole | 15.0 | 19.2 | 19.0 | 17.2 | 14.4 |
| Coke + CH4 sel., % mole | 46.0 | 36.6 | 23.0 | 19.5 | 18.3 |
| C6H6 Yield, % mole | 24.1 | 24.7 | 25.1 | 29.8 | 29.8 |
| C2H4 Yield, % mole | 12.7 | 18.3 | 19.0 | 17.2 | 14.4 |

Comparative Example 10

Comparative example 10 illustrates the results of acetylene conversion in a metallic reactor having an internal diameter of 4 mm using a feed composition containing 20 vol-% methane, 20 vol-% acetylene and 60 vol-% hydrogen.

TABLE 10

| | TEMPERATURE, °C. | | | |
|---|---|---|---|---|
| | 600 | 700 | 840 | 870 |
| Feed Total flow rate, cc/min | 50 | 50 | 50 | 50 |
| C2H2, cc/min | 10 | 10 | 10 | 10 |
| CH4, cc/min | 10 | 10 | 10 | 10 |
| H2, cc/min | 30 | 30 | 30 | 30 |
| Space velocity, $h^{-1}$ | 1534 | 1710 | 1956 | 2009 |
| C2H2 conversion, % mole | 39.9 | 100 | 100 | 100 |
| C6H6 selectivity, % mole | 6.2 | 7.1 | 0.6 | 4.9 |
| C2H4 selectivity, % mole | 2.8 | 4.9 | 0.2 | 2.6 |
| Coke + CH4 sel., % mole | 88.8 | 86.8 | 91.8 | 84.8 |
| C6H6 Yield, % mole | 2.5 | 7.1 | 0.6 | 4.9 |
| C2H4 Yield, % mole | 1.1 | 4.9 | 0.2 | 2.6 |

Example 11

In this example, the variation of feed composition during the acetylene conversion is shown using a mixture of acetylene, methane, hydrogen and carbon dioxide. As can be seen in table 11, high selectivities for benzene and ethylene may be obtained, with a low selectivity for coke fragments and methane.

TABLE 11

| | Temperature, °C. | | | |
|---|---|---|---|---|
| | 915 | 915 | 915 | 915 |
| Feed total flow rate, cc/min | 30 | 30 | 30 | 30 |
| C2H2, cc/min | 4.4 | 6.0 | 4.4 | 4.0 |
| CH4, cc/min | 4.4 | 2.5 | 4.4 | 3.5 |
| H2, cc/min | 17.2 | 15 | 13.2 | 20.5 |
| C02, cc/min | 4.0 | 6.5 | 8.0 | 2.0 |
| Space velocity, h − 1 | 2088 | 2088 | 2088 | 2088 |
| C2H2 conv., % mole | 97.6 | 93.6 | 95.4 | 98.5 |
| C6H6 sel., % mole | 42.1 | 44.0 | 44.6 | 37.2 |
| C2H4 sel., % | 25.3 | 24.6 | 23.6 | 30.9 |
| Coke + CH4 sel., % | 6.9 | 7.1 | 7.3 | 6.5 |
| C6H6 yield, % mole | 41.1 | 41.2 | 42.6 | 36.6 |
| C2H4 yield, % mole | 24.6 | 23.0 | 22.6 | 30.4 |

Example 12

In this example the variation of the feed flow rate during the acetylene conversion using a mixture of acetylene, methane, hydrogen and carbon dioxide is shown. Again, high selectivities of benzene and ethylene are obtained which are significantly better than any results described in the literature or in the comparative examples.

TABLE 12

|  | Temperature, °C. | | |
| --- | --- | --- | --- |
|  | 915 | 915 | 915 |
| Feed total flow rate, cc/min | 30 | 40 | 50 |
| C2H2, cc/min | 4.4 | 6.0 | 7.5 |
| CH4, cc/min | 4.4 | 6.0 | 7.5 |
| H2, cc/min | 13.2 | 17.6 | 22.0 |
| C02, cc/min | 8.0 | 10.4 | 13.0 |
| Space velocity, h − 1 | 2088 | 2785 | 3481 |
| C2H2 conv., % mole | 95.5 | 93.2 | 91.0 |
| C6H6 sel., % mole | 44.6 | 43.0 | 41.1 |
| C2H4 sel., % | 23.6 | 26.2 | 28.9 |
| Coke + CH4 sel., % | 7.3 | 7.0 | 6.9 |
| C6H6 yield, % mole | 42.6 | 40.6 | 37.4 |
| C2H4 yield, % mole | 22.6 | 24.4 | 26.3 |

The features disclosed in the foregoing description or in the claims may, both separately and in any combination thereof, be material for realizing the invention in diverse forms thereof.

The invention claimed is:

1. A process for simultaneous production of benzene and ethylene by conversion of acetylene, comprising the steps:
   (a) supplying a feed composition comprising about 5 to about 30 vol-% acetylene, about 5 to about 30 vol-% methane, about 5 to about 30 vol-% carbon dioxide and about 10 to about 70 vol-% hydrogen into a non-metallic reactor; and
   (b) thermally reacting the feed composition in the reactor at a temperature in the range of about 600 to about 1000° C. to produce a product comprising benzene and ethylene, wherein the reactor is a quartz or ceramic reactor.

2. The process according to claim 1 wherein the feed composition comprises about 10 to about 25 vol-% acetylene, about 10 to about 25 vol-% methane, about 10 to about 25 vol-% carbon dioxide and about 40 to about 70 vol-% hydrogen is supplied into the reactor.

3. The process according to claim 2 wherein the feed composition comprises about 13 to about 18 vol-% acetylene, about 13 to about 18 vol-% methane, about 15 to about 25 vol-% carbon dioxide and about 45 to about 60 vol-% hydrogen is supplied into the reactor.

4. The process according to claim 1 wherein the temperature is in the range of about 800 to about 950° C.

5. The process according to claim 1 further comprising a residence time of the feed composition in the reactor from about 0.5 to about 10 seconds.

6. The process according to claim 1 further comprising a space velocity of the feed composition from about 400 to about 5000 $h^{-1}$.

7. The process according to claim 1 wherein the reactor is a tubular reactor.

8. The process according to claim 7, wherein the tubular reactor has an internal diameter from about 4 to about 15 mm.

9. The process according to claim 1 wherein the process is continuous, semi-continuous or discontinuous.

\* \* \* \* \*